United States Patent [19]

Melpolder

[11] Patent Number: 4,578,357

[45] Date of Patent: Mar. 25, 1986

[54] STABILIZED WATER INDICATING PASTE COMPOSITION

[75] Inventor: Frank W. Melpolder, Wallingford, Pa.

[73] Assignee: Atlantic Richfield Company, Los Angeles, Calif.

[21] Appl. No.: 507,856

[22] Filed: Jun. 27, 1983

[51] Int. Cl.$^4$ .............. C09K 3/00; G01N 33/18; G01N 5/02

[52] U.S. Cl. .................. 436/39; 252/408.1; 73/73; 436/40

[58] Field of Search .......... 436/40, 39, 41, 42; 252/408.1; 73/73, 76, 335

[56] References Cited

U.S. PATENT DOCUMENTS

| | | | |
|---|---|---|---|
| 2,520,993 | 4/1946 | Berger | 436/40 X |
| 2,537,124 | 1/1946 | Earle et al. | 436/39 X |
| 3,505,020 | 4/1970 | Caldwell | 436/40 |
| 3,811,837 | 5/1974 | Hoffman | 436/40 |
| 3,873,271 | 3/1975 | Young | 436/40 |
| 3,898,172 | 8/1975 | Reif et al. | 73/335 X |
| 4,005,132 | 1/1977 | Koster | 436/40 X |
| 4,166,891 | 9/1979 | Elliot | 252/408.1 X |
| 4,255,586 | 3/1981 | Harrington | 556/402 |
| 4,349,509 | 9/1982 | Yoshikawa | 252/408 |
| 4,382,380 | 5/1983 | Martin | 73/73 |

FOREIGN PATENT DOCUMENTS

| | | | |
|---|---|---|---|
| 3007744 | 1/1981 | Fed. Rep. of Germany | 252/408.1 |
| 0124049 | 9/1981 | Japan | 252/408.1 |
| 0131684 | 10/1981 | Japan | 252/408.1 |
| 320581 | 7/1929 | United Kingdom | 436/40 |
| 563182 | 2/1944 | United Kingdom | 436/40 |
| 393291 | 12/1973 | U.S.S.R. | 436/40 |

*Primary Examiner*—John F. Terapane
*Assistant Examiner*—Catherine S. Kilby
*Attorney, Agent, or Firm*—Michael S. Jarosz

[57] ABSTRACT

A visual indicating paste composition for producing a detectable color change upon contact with an aqueous solution comprising an indicator dye capable of changing color in the pH range between about 7 and about 11, an inorganic base in the form of a caustic powder dispersed in a liquid carrier capable of absorbing water which is not rapidly leached by water or hydrocarbon, and a minor amount of a boron-containing compound, is provided. When applied to a measuring probe, the paste composition is particularly adapted for detecting the water level in the bottom of tanks and delivery systems containing gasoline, and especially gasoline containing oxygenated blending components, by producing a clear detectable color change without bleeding or run-off upon contact with an aqueous solution. The paste composition exhibits long shelf life and improved water tolerance.

12 Claims, No Drawings

STABILIZED WATER INDICATING PASTE COMPOSITION

BACKGROUND OF THE INVENTION

1. Field of the Invention

The present invention relates to novel stabilized visual indicating paste compositions and to the utilization of the same to detect the presence, and particularly the level, of aqueous solutions when admixed with hydrocarbons, such as gosoline, oil or other fuel and petroleum fractions. More particuarly, the present invention is concerned with stabilized visual indicating paste compositions which are capable of undergoing a change in color upon contact with aqueous solutions which may be present in minor amounts, generally as a separate phase, in hydrocarbon storage tanks, delivery vehicles, distribution systems, and the like. The compositions of the invention are particularly adapted for use in determining the water level in the bottom of gasoline storage and transportation tanks to determine the amount of water resting in the tank partially filled with the hydrocarbon, and when the water contains oxygenated blending components, such as ethers and alcohols.

2. Description of the Prior Art

Paste compositions detecting the level or presence of water have been disclosed in the prior art. In U.S. Pat. No. 2,520,993, there is disclosed a composition illustrative of such pastes comprising a water soluble cobalt thiocyanate and a finely dispersed filler material having a color other than that of the thiocyanate. Polish Pat. No. 94,388 discloses a paste, which changes color from blue to white or light pink upon contact with water, obtained by blending ammonium thiocyanate with cobalt chloride, an aromatic amine, glycerol, paraffinic oil and ground chalk. Austrian Pat. No. 360,961 discloses a self-adhesive indicator paste useful for detecting pH, nitrate and iron, coated on a polystyrene carrier, which is prepared by impregnating the carrier material with one or more indicator solutions containing Ethyl Red, bromxylenol blue, and acetone.

Pastes for detecting the level of water in hydrocarbon storage tanks, such as gasoline tanks employed at service stations, have been commercially available. In use, such pastes undergo a color change after contacting with water. However, certain of these commercially available pastes are deficient in one or more characteristics, for example, in failing to exhibit a sharp and distinct color change, or alternatively, in having high solubility in the water or hydrocarbon phases, or comparatively short shelf life, or in exhibiting high hygroscopicity. A particular difficulty has been encountered with conventional water indicating pastes when attempts have been made to obtain accurate readings of the water level in tanks and delivery systems for hydrocarbons, such as gasoline, wherein the water contains oxygenated gasoline blending components leached from the gasoline, which components preclude the obtainment of a sharp and distinct color change or cause bleed or run off the measuring probe coated with the paste when contacted with such oxygen-containing aqueous solutions.

In U.S. application Ser. No. 490,744 filed May 2, 1983, of F. W. Melpolder and J. G. Victor entitled "Composition and Probe for Detection of Water," there is disclosed a visual indicating paste composition for producing a detectable color change upon contact with an aqueous solution comprising a water soluble indicator dye capable of changing color in the pH range between about 7 and 11 and an insoluble, inorganic base in the form of a caustic powder dispersed in a liquid carrier capable of absorbing water but which is not rapidly leached by water or hydrocarbon. It has been found, however, that the water indicating paste disclosed in said application, may turn color during storage due to the introduction of trace quantities of water originating from one or more sources. Hence, water may penetrate the paste should humid conditions exist during manufacture or storage of the paste or water may be absorbed by the paste while opening the container during each application of the paste by the user. In addition, water may be introduced with the ingredients, such as liquid carriers, employed in formulation of the paste.

OBJECTS AND SUMMARY OF THE INVENTION

Accordingly, an object of the present invention is to provide a stabilized visual indicating paste which exhibits long shelf life and improved water tolerance, while at the same time being characterized by low solubility in aqueous solutions and hydrocarbons, and good adhesion to substrates to which it is applied.

Another object of the invention is to provide a visual indicating paste for producing a detectable color change upon contact with aqueous solutions without bleeding and which will react rapidly with water but not with any other oxygenated component which may be contained therein, or with the hydrocarbon with which the water is admixed.

Still another object is to provide a probe having coated thereon a stabilized visual indicating composition which is useful for locating the water level of aqueous solutions containing oxygenated blending components in the bottom of tanks and delivery systems containing hydrocarbons such as gasoline, and particularly for indicating sharp and distinct color changes without bleeding or running off the probe.

These and other objects, features and advantages of the invention will be in part obvious and apparent from the specification.

It has now been discovered, after testing a number of combinations of materials, that paste compositions comprised of (i) a dye capable of changing color in the pH range between about 7 and about 11 and (ii) certain inorganic bases dispersed in a liquid carrier, exhibit considerable improvement in shelf life and water tolerance when such paste compositions contain a minor amount of certain boric acid esters or related organic compounds in which the boron is attached to oxygen, as compared with pastes devoid of such boron compounds and/or with commercially available pastes. Further, the paste compositions of the invention produce a sharp and distinct color change, without bleeding, upon contact with water, and particularly, with aqueous solutions containing oxygen-containing organic compounds, such as lower alkanols and ethers. As is noted in the aforementioned application Ser. No. 490,744, the disclosure of which is hereby incorporated by reference, water or aqueous solutions promote the caustic powder-indicator dye color reaction of the paste compositions dissolved therein. It was indeed surprising to discover that certain esters of boric acid and related organic compounds in which boron is attached to oxygen are capable of acting as a water scavanger in such compositions, thereby chemically reacting with water or aqueous solutions prior to the caustic powder-indicator dye color reaction, especially since attempts to employ other added organic compounds including acids, anhydrides, salts, oxides, molecular sieve adsorbents and active metal compounds were all unsuccessful. These compounds failed due to the reaction being either too slow or too active, thereby rendering the caustic powder of the aforementioned paste compositions impotent. Specific examples of failures included adipic acid, stearic acid, maleic anhydride, boric acid, calcium chloride, aluminum isoproproxide and aluminum sulfate.

In accordance with the present invention, any ester of boric acid or anhydride, ortho or meta, or related organic compound in which boron is attached to oxygen, and capable of being hydrolyzed upon contact with water to yield boric acid or a salt thereof, are employable as stabilizers in the paste compositions of the present invention. An additional required characteristic of the boron compounds employable herein is that they be fully miscible with or soluble in the liquid carrier of the paste composition. Any ester, or partial ester, of boric acid, also termed alkoxy- and aryloxy boranes, may be conveniently employed as an ingredient of the composition of the present invention. In general, these boron esters conform to the general formula:

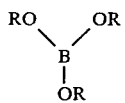 (I)

wherein R taken singly may be the same or different, and may be:
(a) alkyl, primary or secondary, substituted or unsubstituted, having from one to twenty-two carbon atoms, such as ethyl, propyl, hexyl, hexadecyl, stearyl, eicosyl and the like; or
(b) aryl, substituted or unsubstituted, such as tolyl, phenyl, xylyl and the like;
(c) aralkyl, substituted or unsubstituted, having from seven to twenty carbon atoms such as benzyl, phenethyl, 4-methylbenzyl and the like; or
(d) hydrogen;
with the proviso that at least one R be alkyl, aryl or aralkyl. Straight chain trialkyl borates are preferred. Illustrative alkyl borates employable in the paste compositions of the invention include triethyl borate, tripropyl borate, tri-isopropyl borate, trimethylene borate, tri-n-butyl borate, tri-n-hexyl borate, and tri stearyl borate. Tertiary alkyl borates, it has been found, do not provide the stability of the primary and secondary alkyl borates.

Other boron compounds employable in the compositions of the present invention include acyloxyboranes conforming to the general formulae:

wherein R is as defined above. Typical examples of acyloxyboranes employable include acetyloxyborane, hexaoctonoyloxy borane, and oxy-bis(boron acetate) and the like. Another class of boron-containing compounds employable in the compositions of the invention are alkoxyhaloboranes represented by the structures:

$ROBX_2$ (IV)

and $(RO)_2BX$ (V)

wherein R is a primary or secondary alkyl group as above defined and X is a halogen atom such as chlorine and fluorine. Illustrative alkoxyhaloboranes include methyloxydichloroborane, octyloxychlorofluoroborane, and monochlorohexylborate. Polyhydroxylborates such as ethylene glycol biborate, propylene glycol biborate and catechol biborate serve as an example of still another class of boron compounds suitable as constituents of the compositions of the invention.

The boron compound is employed in the paste composition in an amount sufficient to provide the desired stabilization or inhibition to moisture. In general, the boron compound stabilizer is present in the composition of the invention in a concentration ranging from about 0.05 to about 5, preferably between about 0.5 and about 3 percent, by weight of the composition.

The stabilized visual indicating paste compositions of the present invention turn color, generally within about 30 seconds or less, and normally within about 5 to 15 seconds or less, depending upon the indicator dye employed, upon contact with water or an aqueous liquid, i.e., a liquid having aqueous properties, such as water-containing an oxygenated hydrocarbon, including: lower alcohols, illustratively methanol, ethanol, tertiary butyl alcohol, secondary butyl alcohol and mixtures thereof; lower polyols such as alkylene glycols, and lower ketones such as acetone and methyl tertiary butyl ether, and the like. The term "aqueous liquid" is employed herein to designate such substances having chemical characteristics similar to those of water, as distinguished from "oily liquid", i.e. a fuel, petroleum or coaltar hydrocarbon oils and the like, which do not effect a change in color of the composition of the present invention. The aqueous liquids referred to hereinabove may contain up to about 95% of oxygenated hydrocarbon and are typically obtainable from the use of oxygenated blending components in hydrocarbons, such as gasoline, which are leached from the hydrocarbon into the water layer.

The indicator dyes employed in the composition of the present invention are water-soluble dyes which are readily available from commercial sources as fine anhydrous crystalline powders. In general, the dye particles exhibit diameters not greater than about 200 microns. These dyes are characterized as being capable, upon contact with water, of effecting color change of the paste composition in the pH range between about 7 and about 11, preferably between about 8 and about 10. Such dyes are normally employed as components of paste compositions in an amount sufficient to provide the desired color change. In general, such dyes may be employed in concentrations ranging from between about 1 and about 10, preferably between about 4 and about 8 percent, based on the total weight of the paste composition. Representative indicator dyes employable as constituents in the compositions of the invention include: phenolphthalein, o-cresolphthalein, p-naphtholbenzein, ethyl bis(2,4-dinitrophenol) acetate, thymolphthalein, and Nile Blue A (CI51180), it being understood that any dye meeting the aforementioned specifications is employable in the compositions of the invention. If desired, admixtures of these indicator dyes may be employed in amounts ranging from about 1:10 to 10:1, by weight, to achieve a high contrast of color change when the paste composition is employed in an environment requiring an especially high contrasting change, e.g. in storage tanks containing excessive quantities of dirt, rust or other dark colored materials or debris.

The caustic powder employed as a constituent of the visual indicator paste compositions of the present invention must be one which does not dissolve and ionize in the liquid carrier, but is readibly soluble in water. In general, anhydrous solid forms of an alkaline earth oxide, hydroxide, or mixtures thereof, or any compound which will generate an alkaline earth oxide or hydroxide in situ, e.g. an alkaline earth hydride, are suitable for use in such compositions. These materials may be in the form of a finely divided technical grade crystalline powder and are readily available from commercial sources. Typical caustic powders employable in accordance with the invention include calcium oxide, calcium hydroxide, strontium oxide, strontium hydroxide, barium oxide, barium hydroxide, magnesium oxide, magnesium hydroxide, and hydrides of these metals such as calcium hydride. In general, the caustic powder is employed in a concentration ranging from about 1 to about 25 percent, preferably between about 5 and about 20 percent by weight of the composition, in order to provide the desirable water sensitivity properties characteristic of the compositions of the present invention.

As a vehicle for the paste composition of the invention, there is employed a liquid carrier which is capable of absorbing water, but is not readily leached by water or by the hydrocarbon. Any organic compound, or mixture thereof, exhibiting such characteristics and which is inert to the other composition ingredients may be employed. Other required characteristics of the vehicle are that it be characterized by a sufficiently high viscosity for good paste consistency, have a low freezing point and not inhibit fairly rapid, i.e., within about 2 minutes or less, color reaction of the indicator dye, upon contact of the composition with aqueous solutions. Especially suitable liquid carriers employable include aliphatic polyols, alkylene glycols and polyalkylene glycols of sufficiently high molecular weight to preclude their solubility in the water/hydrocarbon environment in which the visual indicating paste composition is employed. In general, the polyols and glycols, or mixtures thereof, having a molecular weight of at least about 75 are useful as liquid carriers in the composition of the present invention. Illustrative polyols employable in the composition of the invention include 1,4-butanediol; 1,3-butanediol; hexylene glycol; 1,2,6-hexanetriol; and 1,6-hexanediol. The polyalkylene glycols normally contain from between about 2 and 4 carbon atoms in each alkylene chain unit of the polyalkylene glycol. Illustrative polyalkylene glycols employable include polyethylene glycol, polypropylene glycol, and polybutylene glycol having molecular weights between about 200 and about 4000. As is evident to those skilled in the art, such polyols and glycols are commercially available products and are employable either alone or as mixtures with or without other conventional liquid carriers, and, when employed as mixtures, are employed to obtain the optimum hydrophilic/hydrophobic balance. In general, the liquid carrier is employed in an amount of at least about 40 percent, and generally between about 50 and about 90 percent, based on the weight of the paste composition. Polyalkylene glycols of molecular weight between about 200 and 1500, employed in an amount of between about 60 and 80 percent of the total weight of the paste composition, provide particularly desirable properties, and hence, are preferred for use in the composition of the invention.

If desired, a gelling agent which serves as a thickner and/or color stabilizer, and which is inert to the ingredients of the composition, may optionally be employed as an added constituent of the paste composition of the invention. The purpose of use of such gelling agent is to retard leaching and to gel the composition. Any known filler having a color other than that which would interfere with the visual detection provided by the paste composition of the invention in its application and which serves to provide the thickening properties and color stabilization indicated may be employed. Illustrative suitable gelling agents employed as components of the composition of the present invention include inert filler or diluents such as talc, clay, diatomaceous earth, calcium silicate, silica, fumed colloidal silica, alumina, pyrophyllite, calcite, or mixtures of the same or other finely divided solid materials. In general, if employed the gelling agent is used in quantities up to about 20 percent, or more, preferably between about 5 and about 15 percent, based on the total weight of the paste composition.

The compositions of the present invention may be prepared by customary methods employed in the art for the production of paste compositions. In general, the components of the composition are conventionally fed to a mixer at ambient temperature and blended to an even, smooth paste, it being understood that blending at elevated temperatures or under other conditions conventionally employed for blending pastes may be employed. Incorporation of the ingredients of the composition is readily effected by incorporation of the solid components, individually or together, by grinding, dry-mixing, or blending into the vehicle. Hence, the insoluble base, indicater dye, boron compound and/or gelling agent, if employed, may be incorporated prior to, concurrently with, or after the incorporation of the other solid ingredients in the vehicle. Alternatively, prior to incorporation of the solid ingredients in the vehicle, the boron compound preferably is dissolved in the vehicle. Since these boron compounds and their hydrolysis products are soluble in the vehicle, these compounds are ideal for drying the vehicle before preparation of the paste and thereafter the boron compound continues to function as a water scavenger during storage and use of the paste.

It is to be understood that the paste composition of the present invention may additionally include adjuvants well-known to those skilled in the art, such as sticking agents, and the like. Hence as sticking agents, there may be employed materials such as casing gelatine, cellulose derivatives such as carboxy-methyl cellulose, sulfite waste liquor, water-dispersable synthetic resins, mineral oil, or equivalent adhesives, all of which are well-known in the art.

The present invention provides readily utilizable stabilized paste compositions which are particularly adapted for locating the water level in tanks or other storage or delivery facilities for hydrocarbons which may be admixed with water, or with "aqueous liquids", as above defined. A particular application of the compositions of the present invention is found in measuring the level of water bottoms in gasoline storage tanks which must be monitored frequently to prevent the delivery of water into vehicle gasoline tanks. Although presently available paste compositions are generally satisfactory for detection of levels of water in tanks; however, water bottoms of storage or delivery facilities for gasoline containing oxygenated blending components, i.e. gasolines containing alcohols or ethers such as methanol, ethanol, tertiary butyl alcohol, methyltertiary butyl ether, or mixtures thereof, may contain up to about 90 volume percent of alcohol in the water level.

The invention may be more fully understood by reference to the following examples:

DESCRIPTION OF THE PREFERRED EMBODIMENTS

Example I

A paste composition comprised of the components indicated in Table I below was prepared:

TABLE I

| Component | Weight Percent |
| --- | --- |
| Phenolphthalein | 7.3 |
| Calcium Oxide | 20.0 |
| Tripropylene Glycol* | 65.9 |
| Fumed Colloidal Silica | 6.8 |
| | 100.0 |

*containing 1.0 weight percent tripropyl borate

The components were fed to a mixer at ambient temperature and blended to a even, smooth colorless paste. Thereafter, the lower end, approximately 4 inches, of a conventionally employed measuring tank gauge was coated with a thin layer of the paste and the probe was lowered to the bottom of a gasoline tank containing unleaded gasoline motor fuel, blended with OXINOL ® 50 blending component comprised of methanol and tertiary butyl alcohol. After holding the gauge to the bottom of the tank for approximately 10 seconds, the gauge was removed from the tank and there was observed a deep red color on the end of the probe showing the depth of the water/alcohol layer.

Example II

A paste composition comprised of the components indicated in Table II, below, was prepared:

TABLE II

| Component | Weight Percent |
| --- | --- |
| Thymolphthalein | 1.4 |
| Calcium Oxide | 21.3 |
| Tripropylene Glycol* | 70.0 |
| Fumed Colloidal Silica | 7.3 |

*containing 1.0 weight percent tripropyl borate

The components were fed to a mixer at ambient temperature and blended to a even, smooth colorless paste. Thereafter, the lower end, approximately 4 inches, of a conventionally employed measuring tank gauge was coated with a thin layer of the paste and the probe was lowered to the bottom of a gasoline tank containing unleaded ed gasoline motor fuel, blended with OXINOL ® 50 blending component comprised of methanol and tertiary butyl alcohol. After holding the gauge to the bottom of the tank for approximately 10 seconds, the gauge was removed from the tank and there was observed a deep blue color on the end of the probe showing the depth of the water/alcohol layer.

Example III

A paste composition comprised of the components indicated in Table III below is prepared:

TABLE III

| Component | Weight Percent |
| --- | --- |
| Phenolphthalein | 9.6 |
| Thymolphthalein | 1.9 |
| Calcium Oxide | 19.2 |
| Polypropylene Glycol 725* | 62.8 |
| Fumed Colloidal Silica | 6.5 |

*containing 0.5 weight percent tripropyl borate

The components were fed to a mixer at ambient temperature and blended to a even, smooth colorless paste. Thereafter, the lower end, approximately 4 inches, of a conventionally employed measuring tank gauge was coated with a thin layer of the paste and the probe was lowered to the bottom of a gasoline tank containing unleaded gasoline motor fuel, blended with OXINOL ® 50 blending component comprised of methanol and tertiary butyl alcohol. After holding the gauge to the bottom of the tank for approximately 10 seconds, the gauge was removed from the tank and there was observed a deep purple color on the end of the probe showing the depth of the water/alcohol layer.

Example IV

Comparative Example

In order to test the stability of the borate containing paste versus the non-inhibited paste, a relative test was developed.

The test employs a constant humidity chamber comprised of a large dessicator with an aqueous slurry of calcium chloride in the lower base. At room temperature the humidity of the enclosed air space remains constant at 33 relative percent. The upper section of the dissicator is separated from the aqueous solution by a shelf having many openings for free circulation of the humidified air. The paste compositions employed in this Comparative Example are identified in Table IV, below:

TABLE IV

| | Weight Percent | |
| --- | --- | --- |
| Component | Inhibited Paste | Noninhibited Paste |
| Phenophthalein | 5.7 | 5.7 |
| Calcium Oxide | 9.0 | 9.0 |
| PolyPropylene Glycol 725 | 46.65 | 47.5 |
| PolyEthylene Glycol 400 | 28.3 | 28.3 |
| Tripropyl Borate | 0.85 | — |
| Fumed Colloidal Silica | 9.5 | 9.5 |
| | 100.0 | 100.0 |

Samples of paste are prepared on microscope slides by placing a small amount of paste on the surface and covering with a circular cover glass. The cover glass is pressed down firmly to spread out evenly the paste film to the edges of the cover glass. The slide is then placed inside the dessicator. In this manner, samples of various paste compositions may be made at the same time for comparative measurement.

Periodically, observations are made of any color changes that may occur due to water absorption from the humidified air. Usually the outermost edge of the inhibited paste will begin to color within the first hour. Thereafter, the progress of color development into the interior takes increasingly longer times. Arbitrarily, the point for comparison is taken as the time required to color the first 0.5 millimeter of the paste film as measured from the leading edge. For the noninhibited paste (i.e. paste devoid of boron compound) the time for 0.5 mm coloration at 75° F. was 6 hours. In contrast, paste inhibited with tripropyl borate required a residence time of 150 hours to reach the same degree of coloration.

While the invention has been illustrated and described and is considered to be the most practical and preferred embodiments, it is recognized that many variations are possible and come within the scope thereof.

I claim:

1. A visual indicating paste composition for producing a detectable color change upon contact with an aqueous solution, said composition exhibiting long shelf life, comprising (i) a water soluble indicator dye capable of changing color in the pH range between about 7 and about 11, (ii) an inorganic base in the form of a caustic powder dispersed in a polyalkylene gylcol liquid carrier selected from the group consisting of an aliphatic polyol, an alkylene glycol, a polyalkylene glycol, and mixtures thereof, and capable of absorbing water but which is not rapidly leached by water or hydrocarbon, (iii) a gelling agent, and (iv) a boron-containing compound which is miscible with or soluble in said carrier and capable of being hydrolyzed upon contact with water to yield boric acid or a salt thereof, present in a moisture inhibiting amount.

2. The composition of claim 1 wherein said base is a member selected from the group consisting of an oxide and a hydroxide of an alkaline earth metal.

3. The composition of claim 2 wherein said liquid carrier comprises at least one polyalkylene glycol containing between 2 and 4 carbon atoms in each alkylene chain unit.

4. The composition of claim 3 wherein said base is finely divided solid calcium oxide.

5. The composition of claim 4 wherein said indicator dye is a member selected from the group consisting of phenolphthalein, o-cresolphthalein, p-naphtholbenzein, ethyl bis(2,4-dinitrophenol) acetate, thymolphthalein, and Nile Blue A (CI51180).

6. The composition of claim 5 wherein the boron-containing compound is a boron ester.

7. The composition of claim 6 wherein said boron ester is a straight chain trialkyl borate.

8. The composition of claim 6 or 7 wherein said boron-containing compound is present in an amount of between about 0.05 and about 5%, by weight of the composition.

9. The composition of claim 6 wherein said indicator dye is phenophthalein, said polyalkylene glycol contains two to four carbon atoms in each unit of the alkylene chain and has a molecular weight of between about 200 and 1500, said gelling agent is fumed colloidal silica and said boron ester is tripropyl borate present in an amount of between about 0.5 and about 3% by weight of the composition.

10. The composition of claim 9 wherein the aqueous solution contains not greater than about 95% of an oxygenated hydrocarbon.

11. A water finding probe comprising a graduated bar coated on at least one end thereof with the composition of claim 1.

12. A water finding probe comprising a graduated bar coated on at least one end thereof with the composition of claim 9.

* * * * *